(12) United States Patent
Wesén et al.

(10) Patent No.: US 10,537,655 B2
(45) Date of Patent: Jan. 21, 2020

(54) DEVICE FOR PROVIDING A VOLUME OF STERILE AIR

(71) Applicant: COMPACTA AB, Lund (SE)

(72) Inventors: Lars Wesén, Lund (SE); Lars Montelius, Lund (SE)

(73) Assignee: COMPACTA AB, Lund (SE)

( * ) Notice: Subject to any disclaimer, the term of this patent is extended or adjusted under 35 U.S.C. 154(b) by 225 days.

(21) Appl. No.: 15/031,542

(22) PCT Filed: Oct. 22, 2014

(86) PCT No.: PCT/EP2014/072684
§ 371 (c)(1),
(2) Date: Apr. 22, 2016

(87) PCT Pub. No.: WO2015/059208
PCT Pub. Date: Apr. 30, 2015

(65) Prior Publication Data
US 2016/0263266 A1   Sep. 15, 2016

(30) Foreign Application Priority Data
Oct. 22, 2013 (SE) ....................... 1351253

(51) Int. Cl.
*A61L 9/20* (2006.01)
(52) U.S. Cl.
CPC ...................... *A61L 9/20* (2013.01)
(58) Field of Classification Search
CPC .................... A61L 9/20; A61L 9/205
See application file for complete search history.

(56) References Cited

U.S. PATENT DOCUMENTS

| 3,511,162 A | 5/1970 | Truhan |
| 3,893,457 A * | 7/1975 | van der Waaij ..... A61G 13/108 128/847 |
| 3,895,570 A * | 7/1975 | Eagleson, Jr. ......... B08B 15/02 454/57 |
| 3,949,656 A | 4/1976 | Lohmann |

(Continued)

FOREIGN PATENT DOCUMENTS

| CN | 201100734 Y | 8/2008 |
| CN | 103148421 A | 6/2013 |
| WO | WO-2011006509 A1 | 1/2011 |

OTHER PUBLICATIONS

International-Type Search Report dated Apr. 22, 2014 for ITS request No. ITS/SE13/00235.

(Continued)

*Primary Examiner* — Donald R Spamer
(74) *Attorney, Agent, or Firm* — Moser Taboada (57) ABSTRACT

The present invention relates to a device and a method for providing a volume of sterile air. The device comprises: a radial fan, at least one particle filter, at least one UV-light generator, and a housing, the housing at least partly enclosing the radial fan, the radial fan being arranged to provide a flow of air in a radial direction towards the housing, the housing being arranged to direct the flow of air in an axial direction, the at least one UV-light generator being arranged to radiate the flow of air with UV-light, and the at least one particle filter being arranged to filter the flow of air, thereby creating the volume of sterile air between the device and the surface.

21 Claims, 3 Drawing Sheets

(56) References Cited

U.S. PATENT DOCUMENTS

| | | | |
|---|---|---|---|
| 4,045,192 A | | 8/1977 | Eckstein et al. |
| 5,830,058 A | * | 11/1998 | Røsjø ................... A61G 13/108 |
| | | | 454/187 |
| 5,961,702 A | * | 10/1999 | Doneit .................... F24F 3/161 |
| | | | 55/355 |
| 5,997,619 A | | 12/1999 | Knuth et al. |
| 6,224,542 B1 | * | 5/2001 | Chang ................ A61B 1/00039 |
| | | | 600/109 |
| 6,500,387 B1 | * | 12/2002 | Bigelow .................. A61L 9/20 |
| | | | 250/432 R |
| 8,128,876 B2 | | 3/2012 | Al-Thallab |
| 2004/0256591 A1 | | 12/2004 | Au et al. |
| 2007/0042702 A1 | | 2/2007 | Jeng et al. |
| 2007/0086912 A1 | * | 4/2007 | Dowling ................. A01M 1/04 |
| | | | 422/1 |
| 2010/0091360 A1 | | 4/2010 | Della et al. |
| 2010/0233010 A1 | | 9/2010 | Al-Thallab et al. |
| 2012/0273720 A1 | | 11/2012 | Kristensson et al. |
| 2013/0192417 A1 | | 7/2013 | Amat et al. |
| 2013/0292571 A1 | * | 11/2013 | Mukherjee .............. G01J 3/108 |
| | | | 250/339.11 |

OTHER PUBLICATIONS

International Search Report dated Mar. 3, 2015 for PCT Application No. PCT/EP2014/072684.

* cited by examiner

DEVICE FOR PROVIDING A VOLUME OF STERILE AIR

TECHNICAL FIELD OF THE INVENTION

This invention relates to a device and method for providing a volume of essentially sterile air.

BACKGROUND

A sterile and particle-free environment is a prerequisite for a diverse range of activities, e.g. when handling certain types of food, when handling laboratory samples, during the production and packaging of certain products, such as e.g. certain medicaments, foodstuffs and integrated circuits, and during surgical operations.

Surgical operations always involve the risk of transmitting potential pathogens to the patient's operation wound. Postoperative wound infections occur in approximately 7% of all surgical operations, and constitute the third most common care-related infection in Sweden. For operations in tissue free from bacteria, the risk of infection is 1-3%. Postoperative wound infections are most often caused by bacteria which contaminate the tissue during the surgical operation. The bacterial contamination may come from the patient himself (endogen infection) or from the surroundings (exogenous infection). Infectious agents may reach the operation wound through the air (air-borne infection) or through contact with e.g. instruments and liquids which have been contaminated during the operation.

Today, most surgical operations need to be carried out in special operating rooms in hospitals. These rooms are provided with ventilation which provides low levels of microorganisms in the air during the surgical operation. In addition, such ventilation minimizes the risk of inflow of microorganisms from the surrounding rooms and cleans the air after the operation. In addition, all personnel present in the operating room need to wear tight clothes to prevent skin particles carrying, potentially harmful, bacteria contaminating the air. Potential sources of contamination of the air in the operating room is e.g. when a door is opened to the operating room or, even more important, when a new person enters the room.

Due to the high demands on the surroundings during a surgical operation, many otherwise lifesaving operations which are performed under conditions where the means for providing sterile conditions are lacking, may result in the patient being infected with a potentially life-threatening infection. Such conditions may be present in disaster areas after e.g. natural disaster, refugee camps, mobile military hospitals or other areas in which the necessary equipment for providing a sterile surrounding is lacking.

During the handling and packaging of certain types of food it is very important not to contaminate the food with potentially harmful micro-organisms, since such microorganisms could lead to severe food poisoning or even intoxications such as botulism. Microorganisms may be a single cell or a multi-cellular organism. Examples of microorganism are bacteria, fungi, yeasts, archaea and protists, viruses and prions.

Samples from patients for laboratory analysis need to be handled with care and the risk of contaminating the sample with microorganisms not originating from the sample must be excluded, since such a contamination could lead to e.g. a patient being wrongly diagnosed with and treated for a disease. In addition, it is also important to reduce the risk of contaminating samples for microbiological analysis of foods for controlling the standards of hygiene in e.g. a restaurant.

Also, it is import not to contaminate medicaments during packaging, since this potentially could destroy the medicament leading to a reduction or even loss of its effect or even lead to the spreading of potentially harmful microorganisms to a patient.

One problem with current so called sterile rooms is that they in fact are not sterile due to the large areas and large amounts of equipment present in the room that needs to be cleaned and sterilized. In addition, as mentioned above, the presence of personnel in the operating room is also a potential risk of contamination. Although extensive cleaning and sterilization measures are taken, a fully sterile environment can never be achieved.

SUMMARY OF THE INVENTION

In view of the above, an objective of the invention is to solve or at least reduce one or several of the drawbacks discussed above. Generally, the above objective is achieved by the attached independent patent claims.

According to a first aspect, the present invention is realized by a device for providing a volume of essentially sterile air comprising a radial fan, at least one particle filter, at least one UV-light generator and, a housing, the housing at least partly enclosing the radial fan. The radial fan is arranged to provide a flow of air in a radial direction towards the housing, the housing being arranged to direct the flow of air in an axial direction such that a peripheral part of the flow has a velocity that is higher than a central part of the flow. The at least one UV-light generator is arranged to radiate the flow of air with UV-light. The at least one particle filter is arranged to filter the flow of air, thereby creating the volume of essentially sterile air. The housing comprises a top portion and a bottom portion, the top portion comprising opposed top wall section extending in a diverging manner towards the bottom portion.

The housing may at least partly enclose the at least one particle filter and the at least one UV-light generator.

The device is advantageous in that it is compact, i.e. it is not space consuming, due to the use of a radial fan. The device can be used to create a volume of essentially sterile air in which a surgical operation can be performed. A procedure which needs to be performed under essentially sterile conditions can be performed in locations where the procedure until now has not been possible to perform, e.g. surgical operation in areas with no access to standard operating rooms. Another advantage is that there no longer is a need of securing that the entire standard operating room and all personnel present in the operating room fulfill the criteria described above. In addition, the device may also be used for creating a volume of essentially sterile air for other applications, such as in the production and packaging of medicaments, in the handling laboratory samples or in the food industry.

The housing may comprise a top portion and a bottom portion, the top portion comprising opposed top wall sections extending in a diverging manner towards the bottom portion.

The device provides an essentially laminar flow of air. Furthermore, the top portion comprising opposed top wall sections extending in a diverging manner towards the bottom portion is advantageous in that the flow of air leaving the periphery of the device has a higher velocity than the flow of air leaving the centre of the device. Thus, the flow of air leaving the periphery of the device, i.e. the peripheral flow, forms a curtain of air having a higher velocity than the air flow enclosed by the curtain, i.e. the air flow leaving the centre of the device. This curtain of air ensures that essentially no non-sterile air can enter the space below the device. The velocity of the peripheral flow being higher than the velocity of the central flow, i.e. the air flow leaving the centre of the device, is advantageous in that it contributes to keeping the volume of essentially sterile air essentially sterile.

The velocity of the peripheral flow being higher than the velocity of the central flow is also advantageous since subject matter subject to the flow of air is less dried. As an example, if the device is used during an operation, the operation surface is less dried and the natural moisture of the operational object is kept. Furthermore, the risk of object being blown away is reduced.

The top wall sections of the housing may be arc shaped. Thus, a cross-section of the top portion may be circular.

The bottom portion of the housing may comprise opposed bottom wall sections extending in parallel. The device may further comprise a plurality of light sources arranged to emit light having a wavelength and an intensity in the axial direction, thus illuminating the volume of essentially sterile air. This is advantageous in that a person using the device has a pleasant working environment. In one embodiment, the device is arranged over a surface and the plurality of light sources arranged to emit light towards the surface.

At least one of the plurality of light source may be directable. These light sources may be directed by, e.g., the surgeon during a procedure, either directly or through an electronic interface. One advantage is that the directable light sources may replace the headlamps which are commonly used today.

At least one of the intensity and the wavelength of light emitted from the light sources may be adjustable. In this way the light may be adjusted to suit each specific application and the light may also be changed during a procedure. In the case of a surgical operation, different kinds of tissue may be visualized by changing the wavelength of the light.

At least one of the plurality of the light sources may comprise a plurality of light emitting diodes. Light emitting diodes are capacity and cost efficient.

The device may further comprise at least one camera for imaging an area under the device and means for transmitting signals from the at least one camera to at least one display. In this way the person performing a task in the volume of essentially sterile air can use the image on a display instead of looking directly at the surface beneath the volume of essentially sterile air. The display may be located on the housing, beside the surface or even remotely located. In this way many persons may follow the procedure. In addition, e.g. a surgeon may perform a surgical operation by remote-controlling an operation robot. In one embodiment, the device is arranged over a surface and the camera is arranged to image the surface.

The device may further comprise means for synchronizing the wavelength of the at least one light source with the at least one camera to obtain an image. In this way, multi-spectral imaging may be achieved. This is especially important, since the human eye perceives three dimensions by interpreting shadows in an image. In addition, different types of tissue, which are more clearly visible when illuminated with a different wavelengths, may be visualized in the same image by superimposing images of the surface illuminated with different wavelengths.

The device may further comprise means for holding at least one tool for use in the volume of essentially sterile air.

The means for holding at least one tool may be equipped with different tools needed for different applications.

The device may further comprise a movable UV-light generator. The movable UV-light generator can be used to sterilize, e.g., instruments which are introduced into the volume of air or to radiate an area of the surface or something arranged on the surface. In addition, if there is a risk of exogenous infection in an operation wound, a limited area of the operation wound may also be sterilized using the movable UV-light generator. The UV-light generator may be held by the means for holding at least one tool.

The device may further comprise at least one shield arranged to be extractable from the device in a direction parallel to the flow of essentially sterile air. In instances where the device is used for operations in open air a slight wind may disrupt the flow of air, and in such instances a shield can be used to maintain the laminar flow of air. The shield may also be used for other purposes, such as limiting the view into the volume of sterile air during for example a surgical operation carried out on a patient who is not anaesthetized. Furthermore, the shield can protect from sunlight.

The device may further comprise guiding means arranged to separate the peripheral flow and the central flow, such that the peripheral flow is arranged to flow between the guiding means and the housing. The guiding means may thus reduce the amount of turbulence inside the housing.

The guiding means may moderate the flow of air to make the transition from the faster flowing peripheral flow to the slower flowing central flow smoother. In addition, the guiding means may cause a higher velocity of the flow of air immediately below the centre of the radial fan, thereby reducing an undertow or backflow of air back into the fan.

The guiding means may be arranged to direct the central flow towards a symmetry axis of the device. In one embodiment, the guiding means has an arched portion contributing to directing the flow of air from the radial fan towards a symmetry axis of the device.

An advantage of a device comprising guiding means according to the present invention is that the flow of air leaving the device has a smoother velocity profile than the flow of air leaving the same device but not comprising the guiding means. In addition, the velocity of the flow of air at the corners of the device may be higher. Furthermore, the number of revolutions per minute can be reduced in a device comprising guiding means according to the present invention as compared to a device according to the present invention but lacking guiding means. This reduction of revolutions per minute can be made without causing a reduction of the effect of the device.

The device may comprise one guiding means.

The device may comprise two guiding means.

The device may comprise three or more guiding means.

The device may further comprise means for detecting pressure of the flow of air before the particle filter, means for detecting pressure of the flow of air after the particle filter, means for calculating a difference between the pressure of the flow of air before the particle filter and the pressure of the flow of air after the particle filter, means for regulating the velocity of the radial fan if the difference between the pressure of the flow of air before the particle filter and the pressure of the flow of air after the particle filter is larger than a predefined value. In this way, an essentially constant velocity of the air flow is ensured, thereby securing that a volume of essentially sterile air is maintained.

The device may further comprise a means for signaling when the particle filter needs to be changed. The means can be arranged to signal if the difference between the pressure of the flow of air before the particle filter and the pressure of the flow of air after the particle filter is larger than a predefined value. This is advantageous in that a user can be reminded to change the particle filter before the permeability is deficient.

The device may be used according to the first aspect in connection with a surgical operation, a procedure of medical treatment, an isolation of a patient, production of medicaments, packaging of medicaments, handling of laboratory samples, handling of matter which is sensitive to contamination with microorganisms and handling of objects which are sensitive to contamination with microorganisms. The advantages of the first aspect are equally applicable to the embodiments of the use. The procedure of medical treatment may be chosen from the group comprising taking care of a wound, intensive care and dentistery. The wound may be an ulcer such as a foot ulcer, leg ulcer, pressure ulcer, varicose ulcer or a diabetic foot. The wound may be a gunshot injury or a stab wound.

In connection with an isolation of a patient, the patient may be protected against airborne microorganisms.

A device according to the present invention may be used in order to locally provide an essentially sterile environment around e.g. a patient to protect the patient from harmful potentially disease-causing microorganisms. Examples of such patients are immunocompromised persons, patients undergoing chemotherapy, premature infants or elderly patients. A plurality of devices according to the present invention may be used in the same space, e.g. a hospital ward, an airplane or a train or in the home of the patient.

It is to be understood that the device may be used also in veterinary applications.

According to a second aspect, the present invention is realized by a method for providing a volume of essentially sterile air. The method comprises a radial fan providing a flow of air in a radial direction towards a housing, the housing directing the flow of air in an axial direction such that a peripheral part of the flow has a velocity that is higher than a central part of the flow, subjecting the flow of air to UV-light, allowing the flow of air to pass a particle filter, thereby creating the volume of essentially sterile air. The advantages of the first aspect are equally applicable to the second aspect. It is to be noted that the second aspect can be equally embodied as the first aspect.

The method may further comprise allowing a plurality of light sources to emit light having a wavelength and an intensity in the axial direction, thus illuminating the volume of essentially sterile air. In one embodiment, the device is arranged over a surface and the plurality of light sources emit light towards the surface.

Other objectives, features and advantages of the present invention will appear from the following detailed disclosure, from the attached claims, as well as from the drawings. It is noted that the invention relates to all possible combination of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

As used herein, the term "microorganisms" is to be interpreted according to its ordinary meaning in the technical field.

Microorganisms may be a single cell or a multi-cellular organism. Examples of microorganism are bacteria, fungi, yeasts, archaea and protists, viruses and prions.

As used herein, the term "comprising" and variations of that term are not intended to exclude other additives, components, integers or steps.

BRIEF DESCRIPTION OF THE DRAWINGS

By way of example, embodiments of the present invention will now be described with reference to the accompanying drawings, in which.

DETAILED DESCRIPTION OF PREFERRED EMBODIMENTS OF THE INVENTION

The present invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

The invention relates to a device for providing a volume of essentially sterile air.

In short, a volume of air transported by a radial fan is subjected to UV-light in order to kill most of the microorganisms in the volume of air, where after the volume of air is filtered through a particle filter in order to capture particles, including bacteria, present in the volume of air. The volume of air leaving the device is essentially sterile and essentially free from particles. This is accomplished due to the laminar flow of the UV-light-treated and filtered air.

It is to be noted that the air can be subjected to UV-light before, during and/or after being filtered through the particle filter.

One embodiment of the invention will now be described in relation to the figures. This embodiment of the invention is described as being intended to be used for creating an essentially sterile volume of air over an operation wound during a surgical operation. However, the skilled person will appreciate that this is an example, and that other applications will be possible, such as handling of laboratory samples, packaging of medicaments or foods, as well as other applications in which an essentially sterile environment is important e.g. in the process industry.

Figure 1:
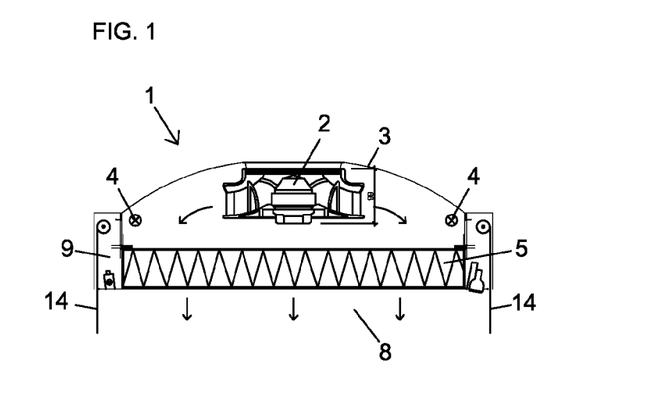
FIG. 1 is a cross-section of a schematic side view of an embodiment of the inventive device.

FIG. 1 illustrates the device 1 comprising a radial fan 2, a housing 3, a UV-light generator 4 and a particle filter 5. A centre of the radial 2 fan may be located on a centre axis of the device 1. The centre axis may also be referred to as a symmetry axis. The radial fan 2 transports a volume of air, thereby creating a flow of air. The radial fan 2 can be any kind of radial fan. Compared to an axial fan, a radial fan is less space consuming and more effective. The radial fan 2 transports air from the surroundings into the housing 3, which encloses the radial fan 2. Air flows from the radial fan 2 in a direction essentially perpendicular to a centre axis of the radial fan 2. Thus, the radial fan 2 accelerates the air essentially radially. Hence, the radial fan 2 changes the direction of the airflow. In other words, the radial fan 2 provides a flow of air in a radial direction. The radial direction can be interpreted as a direction parallel to a radius of the radial fan 2.

The housing 3 is arranged to direct the flow of air in an axial direction. The axial direction can be interpreted as a direction parallel to a rotational axis of the radial fan 2. Thus the flow of air leaving the device 1 flows in a direction essentially parallel to the centre axis of the device.

The flow of air leaving the radial fan 2 in a direction essentially perpendicular to a centre axis of the radial fan 2 is redirected by the curved inner wall of the upper part of the housing 3. This arrangement provides for an essentially laminar flow of air to be directed towards the particle filter 5.

Figure 6:
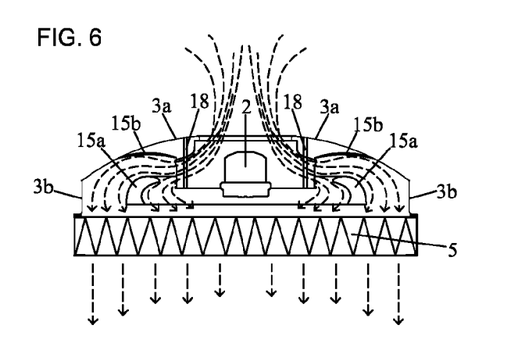
FIG. 6 is a cross-section of a schematic side view of an embodiment of the inventive device.

The housing comprises a top portion 3a and a bottom portion 3b, see FIG. 6. The top portion 3a comprises opposed top wall sections extending in a diverging manner towards the bottom portion 3b. The top wall sections of the housing 3 are arc shaped. The bottom portion 3b of the housing 3 comprises opposed bottom wall sections extending in parallel.

In one embodiment, a horizontal cross section of the top portion 3a of the housing 3 is essentially circular.

In one embodiment, a horizontal cross section of the bottom portion 3b of the housing 3 is essentially quadratic.

In this context, the term "curved" may be defined as a circular arc or a bell-shaped curve.

In this context, the term "rectangular" is to be understood as a four-sided shape having two pairs of parallel lines and that has four right angles. The two pairs of parallel lines may be equal or different. A person skilled in the art realizes that, for e.g aesthetic reasons, the corners of the rectangle may have a rounded shape.

The housing 3 may be of any suitable material such as a carbon-fiber-reinforced polymer, metal or a polymer. The housing 3 is designed to be a combination of a flow and a pressure chamber.

Inside the housing 3, the UV-light generator 4 is arranged to radiate the flow of air in order to kill most of the microorganisms present in the flow of air. UV-light of certain wavelengths is mutagenic to many potentially harmful microorganisms, including bacteria and viruses.

The UV-light generator can comprise at least one mercury lamp. Mercury lamps provide light of a wavelength of 254 nm.

In one embodiment, the UV-light generator comprises at least one light emitting diode (LED) emitting UV-light. A wavelength of the emitted UV-light is in the range of 260-300 nm. In one embodiment, the emitted wavelength is approximately 265 nm. Using UV-LEDs (LEDs emitting UV-light) in the UV-light generator is advantageous in that the UV-LEDs are small, of low weight and capacity efficient.

After being subjected to UV-light, the flow of air is passed through the particle filter 5 in which particles above a certain size are captured. In one embodiment, the flow of air may pass the particle filter 5 before it is subjected to UV-light. Preferably, the particle filter 5 captures particles having a size larger than 0.3 µm. In one embodiment of the invention, the particle filter 5 is a high-efficiency particulate air filter (a HEPA filter), preferably having retention of 99.995% of particles having a size of 0.3 µm. In a specific embodiment, the filter is 600 mm×600 mm.

The volume of air provided by the device is essentially sterile and essentially free from particles. The wording "essentially sterile air" is to be understood as air comprising almost no living microorganisms. The wording "essentially free from particles" is to be understood as air comprising almost no particles. As a reference, the current requirement in Sweden for air in an operating room for certain types of surgery is that the amount of colony forming units (cfu) per $m^3$ must be below 5 cfu/$m^3$.

Figure 2:
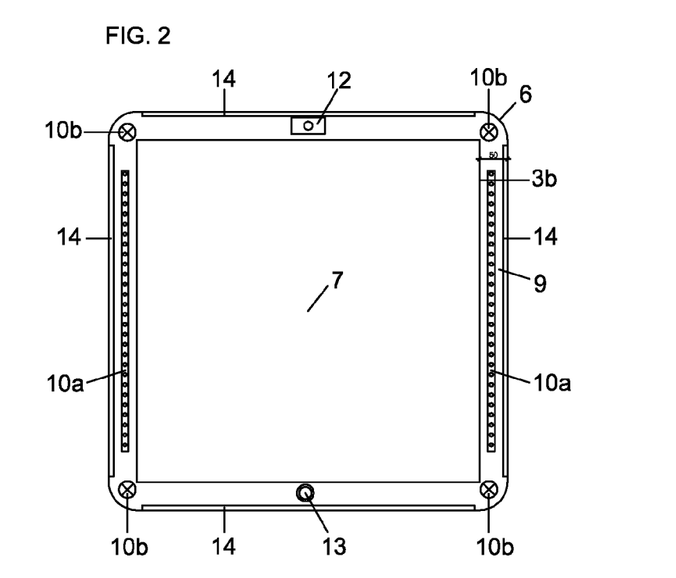
FIG. 2 is a schematic bottom view of an embodiment of the inventive device.

In the embodiment of the invention shown in FIG. 2, the housing 3 comprises means 9 for holding at least one tool. The means 9 for holding at least one tool may be of any suitable material such as a carbon-fiber-reinforced polymer, metal or a polymer.

A plurality of light sources 10 are arranged in the means 9 for holding at least one tool. The light sources 10 can be any type of light source, e.g. light-emitting diodes.

Figure 5:
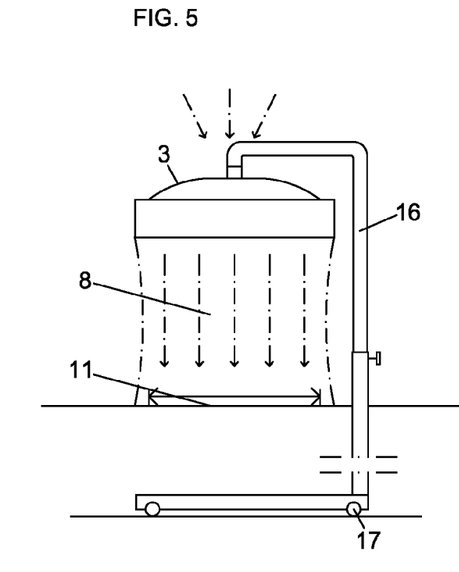
FIG. 5 is a schematic side view of an embodiment of the inventive device.

The light sources are arranged to illuminate a surface 11, see FIG. 5, towards which the volume of air 8 flows. The light sources 10 can emit light of different wavelength and intensity. The light sources can be directable, for example manually or remote-controlled. The light sources can be directable, or adjustable, to provide light in any direction. Some of the light sources 10a emit general or ambient light. Other light sources 10b emit directed light for further illumination of a special area of interest.

The means 9 for holding at least one tool can comprise a camera 12 for capturing images of the surface 11 towards which the volume of air 8 flows. The images can be transmitted to a display which may be located on the housing 3, beside the surface 11 or even remotely located. In the latter case, the surgical operation may be followed by persons, e.g. medical students who are not present in the operating room. In addition, surgeons may be able to perform operations by remote-controlling an operation robot. In one embodiment of the invention, there may be more than one camera 12 and/or more than one display.

Certain types of tissue are seen more clearly when illuminated with light having a certain wavelength. An example is that white light provides poorer reflection in the red wavelength range. Most image acquiring devices area adapted to daylight which provides yellowish images when using flash. Also, filters in image acquiring devices need to be modified. By controlling the light sources 10 to emit light having these different wavelengths and using the camera 12 and display to superimpose the images, all of the selected tissues may be seen in one image presented on the display.

The means 9 for holding at least one tool also can comprise a movable UV-light generator 13. This may be used to manually sterilize e.g. instruments which are introduced into the volume of air 8 or to radiate an area of the surface 11 or something arranged on the surface 11. In addition, if there is a risk of exogenous infection, a limited area of an operation wound can also be sterilized by using the movable UV-light generator 13.

The means 9 for holding at least one tool can also comprise other tools which are necessary for the specific application, such as a small X-ray device, different instruments, such as surgical instruments, equipment for medical monitoring and devices for different kinds of alarms.

Furthermore, the means 9 for holding at least one tool can comprise at least one shield 14 which can be extracted from the device 1 in a direction parallel to the flow of air 8. In instances where the device 1 is used for operations in open air a slight wind may disrupt the flow of air 8, and in such instances a shield can be used to maintain the laminar flow of air 8. The lowering and raising of the shield can be performed manually or controlled by electronics. The shield can comprise, e.g., plastic stripes, solid hard plastic, and/or microfilm which may be transparent.

In one embodiment, the device is provided over a surface. In one embodiment, the part of the housing 3 closest to the radial fan 2 has a circular cross section and the part closest to the particle filter 5 has a rectangular cross section. In one embodiment, the part closest to the particle filter 5 has a quadratic cross section. The inner surface of the housing 3 can be curved in order to give rise to an overpressure in combination with a varied air flow. Thus, a varied controlled air pressure is obtained over the filter. In addition, the inner shape of the housing 3 provides for a means for redirecting the flow of air. Thus after leaving the radial fan 2, the flow of air is redirected by the housing 3 so that the flow of air between the device 1 and the surface has a direction which is essentially parallel to the centre axis of the device 1 and essentially perpendicular to the surface. More particularly, the flow of air leaving the radial fan 2 in a direction essentially perpendicular to a centre axis of the radial fan 2 is redirected by the curved inner wall of the upper part of the housing 3 in such a way that the direction of the flow of air is changed by essentially 90°. Thus, after being redirected by the inner wall of the housing 3, the direction of the flow of air is perpendicular to the central axis and directed towards a surface below the device, i.e. opposite the inlet.

The term "curved" may be defined as a circular arc or a bell-shaped curve.

The air flow that leaves the radial fan 2 is turbulent. The particle filter 5 is arranged to transform the airflow into a laminar air flow. The particle filter 5 being corrugated provides for the conversion of turbulent flow into laminar flow.

The flow of air leaving the device is essentially laminar and has a velocity of at least 0.5 m/s. Preferably, the velocity of the air leaving the device 1 closest to the bottom portion 3b of the housing 3 of the device 1 is larger than the velocity of the air leaving the device 1 at the center 7 (see FIG. 2) of the device 1, since this will ensure that there is a minimal inflow of air from the surroundings. Such an inflow would mean the inflow of non-sterile air in the otherwise essentially sterile volume of air. Preferably, when the cross section of the device 1 is a quadrangle, such as a square or rectangle, the velocity of the air leaving the device 1 at the corners is the highest. The different velocities are created through specific structures present in the interior of the housing 3.

Figure 3:
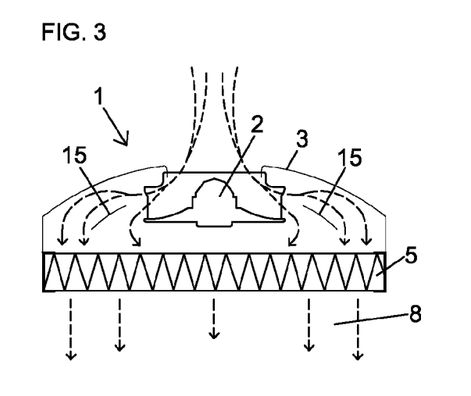
FIG. 3 is a cross-section of a schematic side view of an embodiment of the inventive device.

In one embodiment of the invention shown in FIG. 3 and FIG. 6, the interior of the housing 3 comprises guiding means 15 for guiding the flow of air inside the housing 3 in order to optimize the flow and velocity of the air leaving the device 1. The air leaving the radial fan 2 circulates in the housing 3. The guiding means 15 moderates the flow of air to make the transition from the faster flowing peripheral flow to the slower flowing central flow smoother.

The design of the housing 3 provides a variable pressure over the particle filter 5. The guiding means 15 can, e.g., be curved, straight, or wedge-shaped. The term "curved" may be defined as a circular arc or a bell-shaped curve. As is illustrated in FIG. 6 by guiding means 15 a, the guiding means can have a curved portion. The curved portion is arranged to redirect the flow of air incident on the guiding means, to that it flows towards a symmetry axis of the device.

As is illustrated in FIG. 6, the device may have two guiding means, guiding means 15a, and 15b. The guiding means 15a is equivalent to the guiding means 15 referred to in connection with FIG. 3. Guiding means 15b is arranged to prevent air flowing from the radial fan to flow in a direction away from the particle filter 5. The guiding means 15b is arranged to direct the flow of air leaving the radial fan 2 in a direction towards the housing. In one embodiment, the guiding means 15a and 15b are arranged to direct the flow of air towards the bottom portion 3b of the housing.

In one embodiment of the invention, the guiding means 15 is arranged to even out the velocities of the flow of air leaving the periphery of the device 1 and the flow of air leaving the centre of the device 1. In addition, the guiding means 15 is arranged to distribute the flow of air to essentially the whole area of the particle filter 5. The guiding means 15 may cause the peripheral flow to decrease. Alternatively, the guiding means 15 may cause the parts of the central flow which are closest to the peripheral flow to increase. In addition, the guiding means 15 may cause a higher velocity of the flow of air immediately below the centre of the radial fan 2, thereby reducing an undertow or backflow of air back into the fan 2.

Furthermore, the guiding means 15 may be arranged to reduce the amount of undertow in the flow of air which otherwise may occur at the center of the outlet of air from the radial fan 2. In one embodiment of the invention, the part of the guiding means 15 facing the outlet of the radial fan 2 is curved. An end portion of the guiding means 15 points located closest to the particle filter 5 towards the centre axis of the device. This results in the flow of air being forced in towards the center of the outlet of the radial fan 2.

In one embodiment, the guiding means 15 is arranged in a position wherein a lower part (opposite to the inlet) of the radial fan 3 is located below the upper part of the guiding means 15. The lower part of the radial fan 3 corresponds to about ⅓ of the height of the radial fan 3.

The device 1 can be arranged to hang directly over a surface 11, such as an operation table, or be arranged on a stand 16. The stand 16 may be moveable, e.g. by having wheels 17, as shown in FIG. 5. In addition, the position of the device 1 or the direction of the flow of air may be adjustable in relation to the surface 11. Thus, the flow of air may also flow in directions which are not perpendicular to the surface 11.

The device 1 may also comprise a control system for controlling one or more of fan, UV-light, velocity of the flow of air, direction of the flow of air, intensity of light emitted from at least one of the light sources, wavelength of light emitted from at least one of the light sources, camera, communication between camera and display, position of light source and shield.

In one embodiment of the invention shown in FIG. 6, a bracing 18 is shown. The guiding means 15 and the radial fan 2 are attached to the bracing 18. However, a person skilled in the art realizes that the guiding means 15 and the radial fan 2 can be attached to different bracings.

Figure 7:
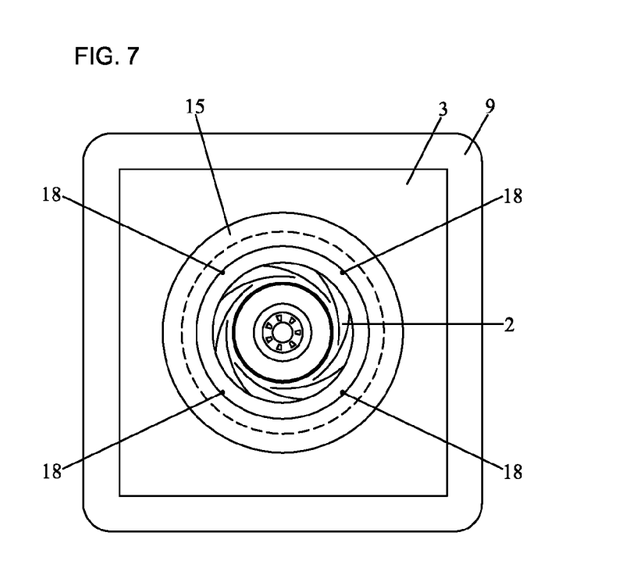
FIG. 7 is a schematic top view of an embodiment of the inventive device.

In one embodiment shown in FIG. 7, the guiding means 15 is attached to the bracing 18 at four points. FIG. 7 also illustrates that the guiding means 15 is arranged around the radial fan 2. In other words, the guiding means 15 extends around the radial fan 2.

Figure 4:
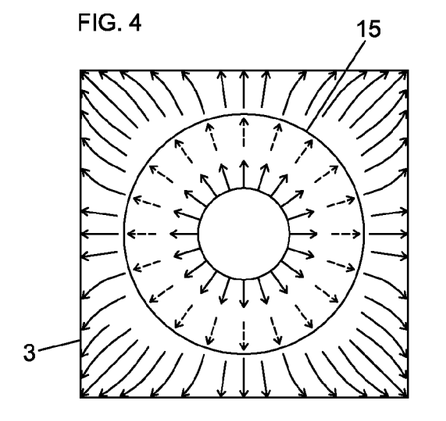
FIG. 4 is a schematic bottom view of an embodiment of the inventive device, showing the flow of air inside the device.

FIG. 4 illustrates the flow of air inside the device. FIG. 4 also illustrates that there is a large flow of air in the corners of the bottom portion of the device.

It will be appreciated that the invention has been illustrated with reference to exemplary embodiments, and that the invention can be varied in many different ways within the scope of the claims.

It should also be noted that the inclusion in the appended claims of some of the numerals used in the figures is purely for illustrative purposes and not to be considered as limiting the scope of the claims.

The invention claimed is:

1. A device for providing a volume of essentially sterile air, the device comprising:
    a radial fan;
    at least one particle filter;
    at least one UV-light generator;
    a housing,
        the housing at least partly enclosing the radial fan,
        the radial fan being arranged to provide a flow of air in a radial direction towards the housing,
        the housing being arranged to direct the flow of air in an axial direction such that a peripheral part of the flow has a velocity that is higher than that of a central part of the flow,
        the at least one UV-light generator being arranged inside the housing to radiate the flow of air and the at least one particle filter with UV-light, and
        the at least one particle filter being arranged to filter the flow of air, thereby creating the volume of essentially sterile air; and
    at least one stationary guiding structure having at least one surface angled with respect to the radial direction, the at least one surface configured to redirect at least a portion of the air flow incident on the at least one surface, towards a central axis of the device.

2. The device according to claim 1, wherein the housing comprises a top portion and a bottom portion, the top portion comprising opposed top wall sections extending in a diverging manner towards the bottom portion.

3. The device according to claim 2, wherein the top wall sections of the housing are arc shaped.

4. The device according to claim 2, wherein the bottom portion of the housing comprises opposed bottom wall sections extending in parallel.

5. The device according to claim 1, further comprising a plurality of light sources arranged to emit light having a wavelength and an intensity in the axial direction, thus illuminating the volume of essentially sterile air.

6. The device according to claim 5, wherein at least one of the plurality of light source is directable.

7. The device according to claim 5, wherein at least one of the intensity and the wavelength of light emitted from the light sources is adjustable.

8. The device according to claim 5, wherein at least one of the plurality of the light sources comprises a plurality of light emitting diodes.

9. The device according to claim 5, further comprising at least one camera for capturing an image of an area under the device, wherein the captured image is transmitted to at least one display.

10. The device according to claim 9, wherein the wavelength of at least one of the plurality of light sources is synchronized with the at least one camera to capture the image.

11. The device according to claim 1, further comprising at least one tool held by the device for use in the volume of essentially sterile air.

12. The device according to claim 1, further comprising a movable UV-light generator configured to irradiate a volume outside the device.

13. The device according to claim 1, further comprising at least one shield arranged to be extractable from the device in a direction parallel to the flow of essentially sterile air.

14. The device according to claim 1, wherein the at least one stationary guiding structure has at least one of a curved, straight or a wedge-shaped profile, and
    wherein the at least one stationary guiding structure is arranged to separate the peripheral part of the flow and the central part of the flow, such that the peripheral part of the flows flows between the at least one stationary guiding structure and the housing.

15. The device according to claim 14, wherein the at least one stationary guiding structure is arranged to redirect the central flow towards the central axis of the device.

16. The device according to claim 1, further comprising a control system for controlling at least one of the radial fan, the velocity of the flow of air, or the direction of the flow of air, wherein
    the velocity of the radial fan is regulated if the difference between the pressure of the flow of air before the particle filter and the pressure of the flow of air after the particle filter is larger than a predefined value.

17. A method for providing a volume of essentially sterile air, the method comprising:
    providing a volume of essentially sterile air, using the device according to claim 1, in at least one of a surgical operation, a procedure of medical treatment, an isolation of a patient, production of medicaments, packaging of medicaments, handling of laboratory samples, handling of matter which is sensitive to contamination with microorganisms, or handling of objects which are sensitive to contamination with microorganisms.

18. The method according to claim 17, wherein the procedure of medical treatment is chosen from a group comprising taking care of a wound, intensive care, and dentistry.

19. The method according to claim 17, wherein the patient is to be protected against airborne microorganisms.

20. A method for providing a volume of essentially sterile air, the method comprising:
    providing, using a radial fan, a flow of air in a radial direction towards a housing, the radial fan and the housing forming part of a device for providing the volume of essentially sterile air;
    directing, using the housing, the flow of air in an axial direction, wherein a peripheral part of the flow has a velocity that is higher than a central part of the flow;
    redirecting, using a stationary guiding structure located in the housing, a portion of the flow of air incident on a surface of the stationary guiding structure towards a central axis of the device;
    passing the flow of air through a particle filter, thereby creating the volume of essentially sterile air; and
    subjecting the particle filter and the flow of air to UV light.

21. The method according to claim 20, further comprising:

illuminating, using a plurality of light sources to emit light having a wavelength and an intensity in the axial direction, the volume of essentially sterile air.

* * * * *